(12) United States Patent  (10) Patent No.: US 9,400,267 B2
Chen et al.  (45) Date of Patent: Jul. 26, 2016

(54) VERSATILE AMBIENT IONIZATION-BASED INTERFACE FOR LC/MS

(71) Applicant: Ohio University, Athens, OH (US)

(72) Inventors: Hao Chen, Athens, OH (US); Yi Cai, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 14/889,625

(22) PCT Filed: Oct. 2, 2013

(86) PCT No.: PCT/US2013/063048
§ 371 (c)(1),
(2) Date: Nov. 6, 2015

(87) PCT Pub. No.: WO2015/009326
PCT Pub. Date: Jan. 22, 2015

(65) Prior Publication Data
US 2016/0123936 A1 May 5, 2016

Related U.S. Application Data

(60) Provisional application No. 61/846,930, filed on Jul. 16, 2013.

(51) Int. Cl.
*G01N 30/72* (2006.01)
(52) U.S. Cl.
CPC .................... *G01N 30/724* (2013.01)
(58) Field of Classification Search
USPC ........................................................ 250/288
See application file for complete search history.

(56) References Cited

U.S. PATENT DOCUMENTS

| 2007/0228271 A1 | 10/2007 | Truche et al. |
| 2008/0314129 A1 | 12/2008 | Schultz et al. |
| 2010/0059674 A1 | 3/2010 | Chen et al. |
| 2011/0253903 A1* | 10/2011 | Sun ................ H01J 49/168 250/426 |
| 2013/0023005 A1 | 1/2013 | Chen et al. |

FOREIGN PATENT DOCUMENTS

EP  2051283 A2  4/2009

OTHER PUBLICATIONS

Sun, X.; Miao, Z.; Yuan, Z.; Harrington, P. B.; Colla, J.; Chen, H. Int. J. Mass Spectrom. 2011, 301, 102-108.
Takats, Z. et al., Anal. Chem. 2004, 76, 4050-4058.
(Continued)

*Primary Examiner* — Kiet T Nguyen
(74) *Attorney, Agent, or Firm* — Wood, Herron & Evans, L.L.P.

(57) ABSTRACT

An apparatus (10) for coupling liquid chromatography with mass spectrometry and for splitting and analyzing a liquid sample includes a fluid conduit (16), which defines a flow passage (18) and is configured to supply the liquid sample. The fluid conduit (16) has an outer surface and a micro-hole (30) through the outer surface into the flow passage (18). The apparatus (10) also includes an ambient ionizer (40) configured to generate and direct a charged solvent (44) toward the micro-hole (30) at the outer surface for ionizing a portion of the liquid sample (32) that emerges out of the micro-hole (30). The apparatus (10) further includes a mass spectrometer (60) having a sample entrance (62) adjacent the micro-hole (30) configured to analyze an ionized portion of the liquid sample (54).

18 Claims, 8 Drawing Sheets

(56) References Cited

OTHER PUBLICATIONS

Takats, Z. et al., Science 2004, 306, 471-473.
Thiam, H. S.; Daud, W. R. W.; Kamarudin, S. K.; Mohammad, A. B.; Kadhuma, A. A. H.; Loh, K. S.; Majlan, E. H. Int. J Hydrogen Energy 2011, 36, 3187-3205.
Vasicek, L. et al., Anal. Chem. 2009, 81, 7876-7884.
Venter, A.R. et aL, Anal. Chem. 2010, 82, 1674-1679.
Wang, H.; Rus, E; Abruna, H. D. Anal. Chem. 2010, 82, 4319-4324.
Wasmus, S. et al., "Real-Time Mass Spectrometric Investigation of the Methanol Oxidation in a Direct Methanol Fuel aell", Journal of the Electrochemical Society, vol. 142, No. 11, Nov. 1995, pp. 3825-3833.
Wiseman, J.M. et al., Angew. Chem. Int. Ed. 2005, 44, 7094-7097.
Wolter, O.; Heitbaum, J. Ber. Bunsen-Ges. Phys. Chem. 1984, 88, 2-6.
Xie, Y. et al., J. Am. Chem. Soc. 2006, 128, 14432-14433.
Xu, X.; Lu, W.; Cole, R. B. Anal. Chem. 1996, 68, 4244-4253.
Zhang, Y. et al., Anal. Chem. 2012, 84, 3838-3842.
Zhang, Y. et al., Chem. Comm. 2011, 47, 4171-4173.
Zhang, Y. et al., Int. J. Mass Spectrom 2010, 289, 98-107.
Zhang, Y. et al., J. Proteome Res. 2011, 10, 1293-1304.
Zhao, W. et al., "Complete Quantitative Online Analysis of Methanol Electrooxidation Products via Electron Impact and Electrospray Ionization Mass Spectrometry", Analytical Chemistry, vol. 84, No. 13, Jul. 3, 2012, pp. 5479-5483.
Zhao, W. et al., "Quantitative Online Analysis of Liquid-Phase Products of Methanol Oxidation in Aqueous Sulfuric Acid Solutions Using Electrospray Ionization Mass Spectrometry", Analytical Chemistry, vol. 82, No. 6, Mar. 15, 2010, pp. 2472-2479.
Zhao, W. et al., "Quantitative Online Detection of Volatile and Nonvolatile Methanol Electrooxidation Products by combined Electron Impact Mass Spectrometry and Electrospray Ionization Mass Spectrometry", ECS Transactions, vol. 35(12), 2011, pp. 9-19.
Zhou, F.; Van Berke, G. J. Anal. Chem. 1995, 67, 3643-3649.
Zubarev, R.A. et al., J. Am. Chem. Soc. 1998, 120, 3265-3266.
Aebersold, R. et al., Chem. Rev. 2001, 101, 269-296.
Bai, H.; Ho, S. W. Polym. Int. 2011, 60, 26-41.
Becker, J.S. et al., Int. J. Mass Spectrom. 2003, 228, 985-997.
Bogialli, S. et al., "Confirmatory analysis of sulfonamide antibacterials in bovine liver and kidney: extraction with hot mater and liquid chromatography coupled to a single- or triple-quadrupole mass spectrometer ", Rapid Communications in Mass Spectrometry, vol. 17, No. 11, Jun. 15, 2003, pp. 1146-1156.
Bond, A. M.; Colton, R.; D'Agostino, A.; Downard, A. J.; Traeger, J. C. Anal. Chem. 1995, 67, 1691-1695.
Childers, C. L.; Huang, H.; Korzeniewski, C. Langmuir 1999, 15, 786-789.
Chowdhury, S.K. et al., J. Am. Soc. Mass Spectrom. 1990, 1, 382-388.
Chrisman, P.A. et al., J. Am. Soc. Mass Spectrom. 2005, 16, 1020-1030.
D.R., P.; L.M., R. Polymer 2008, 49, 3187-3204.
Denes, J. et al., Anal. Chem. 2009, 81, 1669-1675.
Dixon, R.B. et al., J. Am. Soc. Mass Spectrom. 2007, 18, 1844-1847.
Djilali, N. Energy 2007, 32, 269-280.
Fenn, J.B. et al. Science 1989, 246, 64-71.
Ferguson, C.N. et al., Anal. Chem. 2011, 83, 6468-6473.
Gronborg, M. et al., Mol. Cell Proteomics 2002, 1, 517-527.
Hartmanova, L. et al., "Fast profiling of anthocyanins in wine by desorption nano-electrospray ionization mass spectrometry", Journal of Chromatography A, vol. 1217, No. 25, Jun. 1, 2010, pp. 4223-4228.
Hu, L. et al., Angew. Chem. 2011, 123, 4219-4222; Angew. Chem. Int. Ed. 2011, 50, 4133-4136.
Hunter, T., Cell 2000, 100, 113-127.
International Preliminary Report on Patentability in International Patent Application No. PCT/US2013/068922, mailed May 12, 2015, 10 pgs.
International Preliminary Report on Patentability in International Patent Application No. PCT/US2013/068925, mailed May 12, 2015, 8 pgs.
International Search Report and Written Opinion in International Patent Application No. PCT/US2013/063048, mailed May 3, 2014, 8 pgs.
International Search Report and Written Opinion in International Patent Application No. PCT/US2013/068922, mailed Feb. 11, 2014, 14 pgs.
International Search Report and Written Opinion in International Patent Application No. PCT/US2013/068925, mailed Mar. 19, 2014, 11 pgs.
Iwasita-Vielstich, T. Advances in Electrochemical Science and Engineering; VCH Verlagsgesellschaft: Weinheim: Germany, 1990.
Jusys, Z.; Massong, H.; Baltruschat, H. J. Electrochem. Soc. 1999, 146, 1093-1098.
Kharlamova, A. et al., J. Am. Soc. Mass Spectrom. 2011, 23, 88-101.
Krasny, L. et al., "In-situ enrichment of phosphopeptides on MALDI plates modified by ambient ion landing", Journal of Mass Spectrometry, vol. 47, No. 10, Oct. 27, 2012, pp. 1294-1302.
Kweon, H.K. et al., Anal. Chem. 2006, 78, 1743-1749.
Lane, A. et al., Proc. Natl. Acad. Sci. USA 2009, 106, 7314-7319.
Leuthold, L. A.; Mandscheff, J. F.; Fathi, M.; Giroud, C.; Augsburger, M.; Varesio, E.; Hopfgartner, G. Rapid Commun. Mass Spectrom. 2006, 20, 103-110.
Li, J. J et al., "Online Coupling of Electrochemical Reactions with Liquid Sample Desorption Electrospray Ionization-Mass Spectrometry", Analytical Chemistry, vol. 81, No. 23, Dec. 1, 2009, pp. 9716-9722.
Lu, M. et al., Anal. Bioanal. Chem. 2012, 403, 355-365.
Ma, X. et al., Anal. Chem. 2008, 80, 6131-6136.
McLachlin, D.T. et al., Curr. Opin. Chem. Biol. 2001, 5, 591-602.
Miao, Z. et al., Anal. Chem. 2011, 83, 3994-3997.
Miao, Z. et al., J. Am. Soc. Mass Spectrom. 2009, 20, 10-19.
Miao, Z. et al., J. Am. Soc. Mass Spectrom. 2010, 21, 1730-1736.
Ota, K. I.; Nakagawa, Y.; Takahashi, M. J. Electroanal. Chem. 1984, 179, 179-186.
Pan, N. et al., "Highly efficient ionization of phosphopeptides at low pH by desorption electrospray ionization mass spectrometry", The Analyst, vol. 138, No. 5, Jan. 1, 2013, p. 1321.
Permentier, H. P.; Bruins, A. P. J. Am. Soc. Mass Spectrom. 2004, 15, 1707-1716.
Permentier, H. P.; Jurva, U.; Barroso, B.; Bruins, A. P. Rapid Commun. Mass Spectrom. 2003, 17, 1585-1592.
Perry, R.H. et al., Angew. Chem. 2011, 123, 264-268; Angew. Chem. Int. Ed. 2011, 50, 250-254.
Porath, J. et al., Nature 1975, 258, 598-599.
Posewitz, M.C. et al., Anal. Chem. 1999, 71, 2883-2892.
Poulter, L. et al., Biochim. Biophys. Acta 1987, 929, 296-301.
Qiu, B. et al., "Desorption electrospray ionization mass spectrometry of DNA nucleobases: implications for a liquid film model", Journal of Mass Spectrometry, vol. 44, No. 5, May 1, 2009, pp. 772-779.
Roussel, C.; Dayon, L.; Lion, N.; Rohner, T. C.; Josserand, J.; Rossier, J. S.; Jensen, H.; Girault, H.H. J. Am. Soc. Mass Spectrom. 2004, 15, 1767-1779.
Salih, E, Mass Spec. Rev. 2005, 24, 828-846.
Song, C. Catal Today 2002, 77, 17-49.
Steele, B. C. H.; Heinze!, A. Nature 2001, 414, 345-352.

* cited by examiner

VERSATILE AMBIENT IONIZATION-BASED INTERFACE FOR LC/MS

RELATED APPLICATIONS

This application claims the benefit of U.S. Provisional Patent Application Ser. No. 61/846,930, entitled VERSATILE AMBIENT IONIZATION-BASED INTERFACE FOR LC/MS, filed on Jul. 16, 2013, the disclosure of which is incorporated herein by reference in its entirety.

TECHNICAL FIELD

The present invention is related to an apparatus for coupling liquid chromatography with mass spectrometry and a method of using the same.

BACKGROUND

Mass spectrometry (MS) with atmospheric pressure ionization techniques, such as electrospray ionization (ESI) or atmospheric pressure chemical ionization (APCI), coupled with liquid chromatography (LC) has become one of the most powerful techniques for the analysis of biomolecules and pharmaceuticals. In numerous laboratories around the world, LC/MS combined technique has been a valuable implementation.

The techniques for coupling LC with MS have become diversified with increased capability of LC/MS. Desorption electrospray ionization (DESI), which was originally developed by Professor Graham Cooks et al. from Purdue University, has been introduced for direct sample ionization with little or no sample preparation. In addition to analysis of solid samples, DESI's use has been extended for direct liquid sample analysis.

Splitting eluent in an LC/MS experiment is often necessary when the mobile phase flow rate is too high for MS ionization. For instance, ESI requires an optimal sample infusion rate at a μL/min level, whereas a mobile phase flow rate for chromatographic separation using regular analytical LC columns is in the range of approximately 1-2 mL/min. Even higher flow rates (up to 9 mL/min) are needed for ultra-fast LC separation using monolithic columns. In addition, post-LC column splitting is needed when a remaining portion of LC eluent after MS detection needs to be collected for a preparative purpose.

Typically, post-LC column splitting of LC eluent can be made using a Tee splitter in which one of the split eluent streams goes to a mass spectrometer for detection and the other may go to waste or to a second detector. However, a connection capillary bridging the Tee and MS, as well as the Tee splitter itself, introduces dead volume and may cause peak broadening. Furthermore, the flow rate of the eluent flowing into the mass spectrometer is significantly reduced after splitting (e.g., the flow rate can be dropped by 100 times from 1 mL/min to 10 μL/min after splitting). Both factors contribute to a long time delay for MS detection. Therefore, using a Tee, it is difficult to collect LC analytes in the other "waste" stream because the analytes in the "waste stream" could flow out of the LC/MS apparatus prior to split eluent being detected by MS. In addition, the introduced dead volume will lead to peak broadening. Moreover, use of a post-column Tee splitter increases LC column back pressure. Thus, a new LC/MS interface that allows splitting LC eluent for both fast online MS detection and online sample collection without introducing significant dead volume and back pressure is desired.

SUMMARY

In one illustrative embodiment of the present invention, an apparatus for analyzing a liquid sample is described. The apparatus includes a fluid conduit for defining a flow passage and configured to supply the liquid sample, for example, from an LC column. The fluid conduit has an outer surface and a micro-hole through the outer surface into the flow passage. The apparatus further includes an ambient ionizer configured to generate a charged solvent and to direct the charged solvent toward the micro-hole at the outer surface. The apparatus still further includes a mass spectrometer having a sample entrance adjacent the micro-hole. The apparatus, built based on the new splitting methodology and ambient ionization technique, provides for nearly real-time monitoring of LC eluent and online collection of LC-separated analytes, while reducing or preventing introduction of dead volume and back pressure.

In another illustrative embodiment, a method of analyzing a liquid sample includes supplying the liquid sample through a fluid conduit having an outer surface, a flow passage, and a micro-hole through the outer surface into the flow passage, such that a first portion of the liquid sample exits the fluid conduit through the micro-hole and a second portion of the liquid sample continues through the fluid conduit. The method further includes directing a charged solvent to the first portion of the liquid sample toward the micro-hole at the outer surface, thereby ionizing the first portion of the liquid sample to form an ionized portion; directing the ionized portion to a mass spectrometer; and collecting the second portion of the liquid sample without ionizing the second portion.

The objects and advantages of the present invention will be further appreciated in light of the following detailed description and drawings provided herein.

BRIEF DESCRIPTION OF THE DRAWINGS

The accompanying drawings, which are incorporated in and constitute a part of this specification, illustrate embodiments of the invention and, together with a general description of the invention given above and the detailed description given below, serve to explain the principles of the invention.

DETAILED DESCRIPTION

Figure 1:
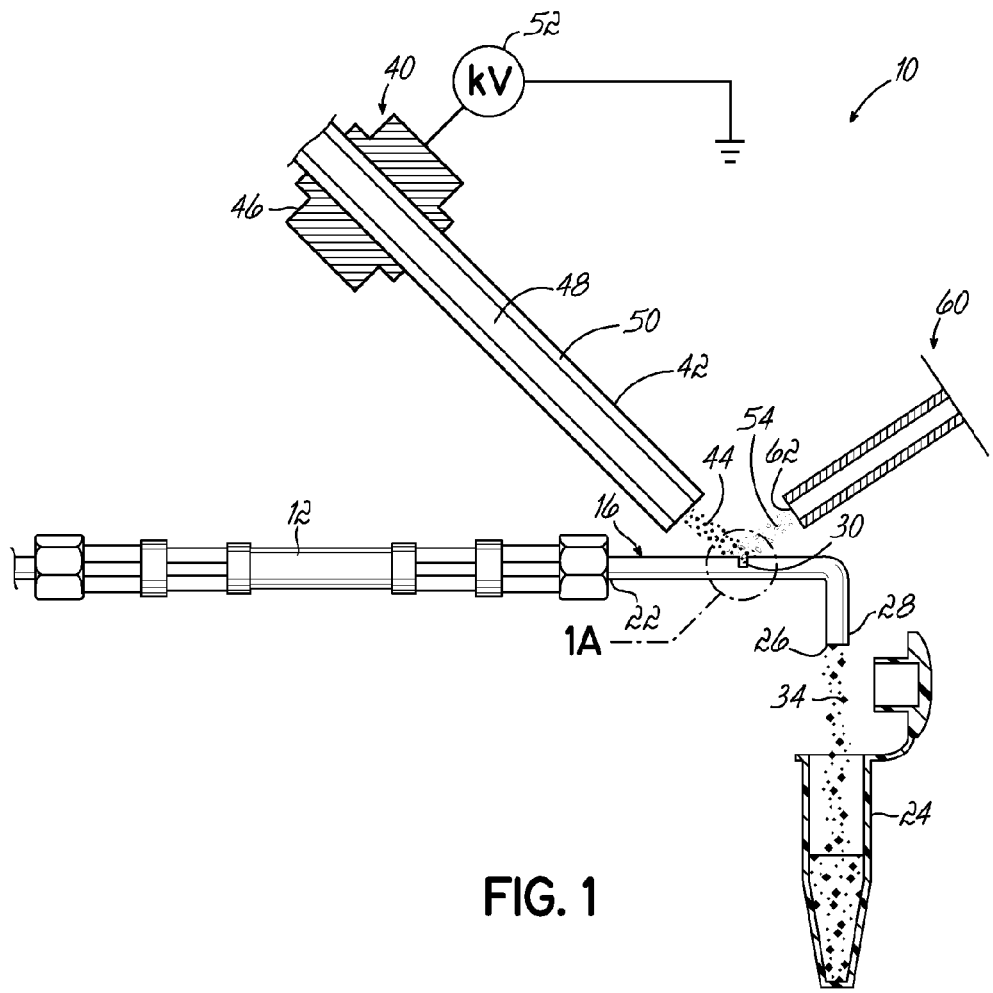
FIG. 1 is a diagrammatic cross sectional view of an embodiment of the present invention.

Briefly, FIG. 1 illustrates an apparatus 10 having an ambient ionization-based interface for LC/MS according to an embodiment of the present invention. The apparatus 10 has a new splitting interface for LC/MS applications with fast DESI ionization capability, which allows MS monitoring of LC eluent with minimal time delay (in milliseconds) and reduced back pressure, as well as online collection of LC-separated analytes for preparation purposes.

More specifically, a liquid sample is processed through an LC column 12, which outputs an eluent 14 containing LC-separated analytes. The LC column 12 may comprise a reversed phase column, a normal phase column, a monolithic column, a size-exclusion column, an ion exchange column, or an ultra performance liquid chromatography (UPLC) column, for example. An output of the LC column 12 is coupled to a fluid conduit 16, which has an outer surface and a flow passage 18 in an interior of the fluid conduit 16. The flow passage 18 is configured to supply a liquid sample of the eluent 14 to a liquid sample collector (described in further detail below).

Figure 1A:
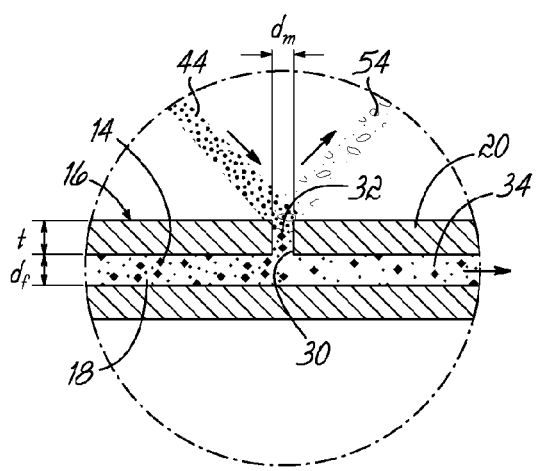
FIG. 1A is a magnified view of a portion of the apparatus of FIG. 1 at encircled area 1A.

The fluid conduit 16 may comprise a tube constructed from a non-reactive material, such as polyaryletheretherketone (PEEK) or stainless steel, for example. As shown in FIG. 1A, the flow passage 18 has an inner diameter $d_f$ ranging, for example, from approximately 10 μm to approximately 1000 μm. Specifically, the flow passage 18 may have an inner diameter $d_f$ of approximately 510 μm. Walls 20 of the fluid conduit 16 have a thickness t ranging from approximately 10 μm to approximately 1000 μm. Specifically, the walls 20 may have thickness t of approximately 530 μm. With reference again to FIG. 1, the fluid conduit 16 may have a length of approximately 1 cm to approximately 5 cm. The LC column 12 is coupled to one end 22 of the fluid conduit 16, and a liquid sample collector 24 is positioned near an outlet 26 at opposite end 28 of the fluid conduit 16.

The liquid sample collector 24 may comprise a vial, test tube, or any other container sufficient to hold a quantity of the liquid sample eluent 14. Alternatively, the liquid sample collector 24 may comprise an apparatus for introducing the quantity of the liquid sample eluent 14 into another analyzer or detector (not shown).

A micro-hole 30 is positioned in the fluid conduit 16 downstream of the LC column 12. In an embodiment, the micro-hole 30 may be horizontally positioned approximately 1 mm to approximately 3 cm downstream of the LC column 12. The micro-hole 30 may be drilled through the wall 20 of the fluid conduit 16. A length of the micro-hole 30 is equivalent to the thickness t of the fluid conduit wall 20. In this way, the micro-hole 30 is a small passage or channel through the fluid conduit wall 20. As such, the micro-hole 30 runs through the outer surface of the fluid conduit 16 into the flow passage 18. The micro-hole 30 may have an inner diameter $d_m$ of approximately 10 μm to approximately 350 μm. The inner diameter $d_m$ of the micro-hole 30 may be greater than or less than the inner diameter $d_f$ of the flow passage 18.

When the LC eluent 14 flows through the fluid conduit 16, a small aliquot or portion of LC eluent 32 emerges out of the fluid conduit 16 from the micro-hole 30. The portion of the LC eluent 32 that emerges through the micro-hole 30 may be ionized and subjected to MS, as described in further detail below. The remaining LC eluent 34 inside the fluid conduit 16 (i.e., a portion of the LC eluent 14 that does not exit through the micro-hole 30), continues through the fluid conduit 16 and exits the fluid conduit 16 at the outlet 26. The remaining LC eluent 34 is then collected in the liquid sample collector 24. In this way, the LC eluent 14 is effectively split into a portion 32 that is subject to ionization and MS and a remainder 34 that is collected or introduced into another analyzer or detector (not shown) for analysis or characterization.

The relative sizes of the inner diameter $d_f$ of the flow passage 18 and the inner diameter $d_m$ of the micro-hole 30 influence a splitting ratio of the portion of the LC eluent 32 that exits through the micro-hole 30 to the remainder of the LC eluent 34 that is collected. For example, the splitting ratio may range from approximately 4:96 (i.e., a 96% collection yield when the $d_m$ is 100 μm) to approximately 3:7 (i.e., a 70% collection yield when the $d_m$ is 100 μm).

The portion of the LC eluent 32 that exits through the micro-hole 30 may be subjected to ambient ionization—such as DESI, DART, high energy particles (i.e., ions, atoms, or molecules) ionization, or laser desorption ionization, for example—and MS. An LS-DESI-MS system is described in detail in U.S. Pat. Nos. 7,915,579 and 8,330,119, the disclosures of which are incorporated in their entireties herein by reference. In the apparatus 10 shown in FIG. 1, an ambient ionizer 40 having a spray probe 42 generates microdroplets of a charged solvent 44 and directs the charged solvent 44 toward the micro-hole 30. An outlet of the ambient ionizer 40 may be positioned approximately 0.5 cm to approximately 1 cm from the micro-hole 30. The charged solvent 44 ionizes the portion of the liquid eluent 32.

In an embodiment, the ambient ionizer 40 may be a DESI apparatus that includes a housing 46 having a solvent conduit 48 surrounded by a gas conduit 50. A voltage generator 52 is attached to the housing 46 and is operable to charge the solvent within the solvent conduit 48. The DESI apparatus generates a nebulized, charged solvent 44 that ionizes the portion of the liquid eluent 32 by desorption. The DESI apparatus may operate at a flow rate of approximately 1 μL/min to approximately 100 μL/min. However, it would be understood that any ambient ionizer 40 apparatus could be used to effect DART, laser desorption ionization, electrosonic spray ionization (ESSI), or high energy particle ionization, for example. A voltage generator 52 is attached to the housing 46 and is operable to charge the solvent within the solvent conduit 48.

The spray impact of the microdroplets of charged solvent 44 from the spray probe 42 with the portion of the LC eluent 14 that emerges from the micro-hole 30 ionizes and deflects an ionized portion of the LC eluent 54 into a mass spectrometer 60. The mass spectrometer 60 having a sample entrance or opening 62 is also positioned near the micro-hole 30. For example, the opening 62 may be positioned approximately 0.5 cm to approximately 2 cm from the micro-hole 30. The ionized portion of the LC eluent 54 enters the opening 62, where a pump (not shown) maintains the atmosphere in the mass spectrometer as a vacuum. The mass spectrometer 60 analyzes a mass-to-charge ratio of the ionized portion of the LC eluent 54, as described in U.S. Pat. Nos. 7,915,579 and 8,330,119.

In use, a liquid sample is supplied through an LC column 12 and through a fluid conduit 16 coupled thereto. The fluid conduit 16 has a micro-hole 30 positioned therein, and a portion of the liquid sample (i.e., a portion of the LC eluent 32) exits the fluid conduit 16 through the micro-hole 30. An ambient ionizer 40 generates a charged solvent 44 that is directed to the portion of the LC eluent 32 that exits the fluid conduit 16 through the micro-hole 30. The charged solvent 44 ionizes the portion of LC eluent 32. The ionized portion of LC eluent 32 is directed to the mass spectrometer 60 for mass-to-charge ratio analysis. The remainder of the LC eluent 34 that does not exit the liquid conduit 16 through the micro-hole 30 flows out through the outlet 26 of the fluid conduit 16 into a liquid sample collector 24. Because the remainder of the LC eluent 34 remains in the fluid conduit 16, rather than being subjected to the charged solvent 44 generated by the ambient ionizer 40, the remainder of the LC eluent 34 that is collected as a sample has not been ionized.

The configuration of the interface between the LC column 12 and the mass spectrometer 60 allows for fast MS detection of analytes after LC separation. For example, a liquid DESI interface may be used to couple with high performance liquid chromatography (HPLC), in which the eluent 14 with a high flow rate up to 1.8 mL/min can be directly sampled and ionized by DESI-MS. As DESI is able to ionize LC eluent 14 from the fluid conduit 16 as soon as it emerges out of the micro-hole 30, no extra connection conduit as used in the traditional splitter for ESI ionization is necessary. A time delay for LC eluent 14 to pass through the micro-hole 30 is negligible. For example, the LC eluent 14 may pass through the micro-hole 30 in less than or equal to approximately 10 ms. More specifically, the LC eluent 14 may pass through the micro-hole 30 in less than or equal to approximately 6 ms. Therefore, DESI-MS used with this interface offers almost real-time monitoring of the LC eluent 14. Thus, the occurrence of peak broadening may be avoided or reduced, and high detection sensitivity may be achieved.

Moreover, reactive DESI can be used for derivatization, for example, for supercharging or signal enhancement of protein ions. The derivation by reactive DESI, in contrast to traditional derivatization protocol used for LC/ESI-MS coupling, would not introduce extra dead volume as the derivatization occurs during ionization process.

Another benefit of the apparatus 10 of the present invention is its ability to perform MS detection before or concurrently with the collection of the remainder of LC eluent 34 (i.e., isolated sample analyte). It thus expands the application of preparative liquid chromatography.

Yet another benefit of the apparatus 10 of the present invention is its ability to be compatible with various liquid chromatography columns, such as monolithic columns, in which a high flow rate of the mobile phase is used to achieve ultra-fast separation in a few minutes.

The following examples illustrate particular properties and advantages of some of the embodiments of the present invention.

Example 1

An apparatus 10 for LC/DESI-MS was built. A PEEK tube 16 having an inner diameter $d_f$ of 510 µm, a wall thickness t of 530 µm, and a length of 5 cm was connected to an outlet of an LC column 12. The PEEK tube 16 included a micro-drilled hole 30 having an inner diameter $d_m$ of 350 µm and a length of 530 µm. The micro-hole 30 was located 3 cm downstream from the LC column 12 and 2 cm upstream from an outlet 26 of the PEEK tube 16. An end 28 of the PEEK tube 16 was slightly bent downward, such that gravity facilitated sample collection. A portion of sample eluent 32 flowing out of the micro-hole 30 underwent interactions with microdroplets of charged solvent 44 generated from a DESI spray probe 42 for ionization at the surface of the PEEK tube 16. With a mobile phase flow rate of 1.0 mL/min, the splitting ratio of the portion of the LC eluent 32 emerging out of the PEEK tube 16 micro-hole 30 relative to a remainder of the LC eluent 34 exiting the tube outlet 26 was 3:7. In other words, under this circumstance, 30% of the LC eluent 14 was subject to DESI-MS analysis and 70% of the LC eluent 14 was collected.

For the protein mixture separation, a Waters XB Bridge™ 300 C4 column (3.5 µm, 4.6 mm×150 mm) was employed with ACN:H₂O:TFA (30:70:0.1 by volume) used as the mobile phase. For the saccharide mixture separation, an Agilent ZORBAX ODS column was also adopted with 0.1% FA in H₂O used as the mobile phase. A 20 µL injection loop was used for sample loading.

The spray solvent for DESI was CH₃OH/H₂O/HOAc (50:50:1 by volume) with or without supercharging reagent, 3-nitrobenzyl alcohol (m-NBA), and was injected at a flow rate of 10 µL/min with a high voltage of 5 kV applied to the spray solvent.

A Thermo Finnigan LCQ DECA ion trap mass spectrometer 60 (Thermo Scientific, San Jose, Calif.) was employed for ion detection.

For comparison, ESSI, a variant form of ESI that employs an ESI source with supersonic nebulization gas for better desolvation effect, was used to detect the LC-separated analytes after the eluent splitting with an ASI adjustable commercial splitter. The sheath gas pressure used for ESSI was 120-160 psi, and a high voltage of 5 kV was applied for ionization. In this study, the collected samples after LC separation and DESI-MS detection were subjected to direct ESSI-MS analysis to check the purity of the collected sample.

Figures 1, 2A:
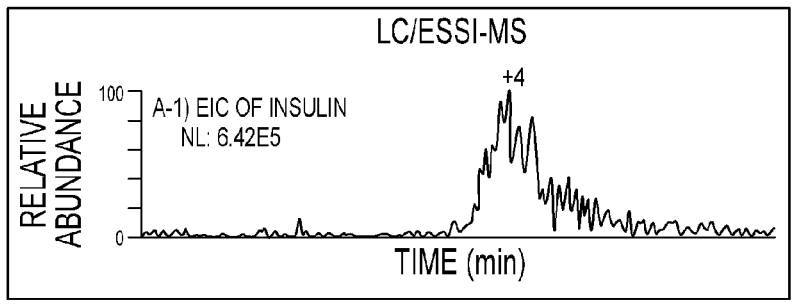
FIGS. 2A-2D-2 are extracted ion chromatograms showing the results of the experiment of Example 1.
Figures 1, 2B:
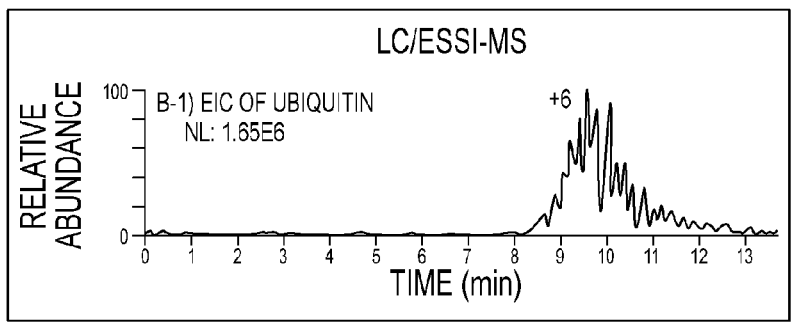

A protein mixture and a saccharide mixture were chosen as examples for demonstration of the versatility of the LC/DESI-MS 10, specifically, the fast detection capability of DESI and convenient sample collection after LC/MS analysis. First, for the protein separation detection and collection, a reversed phase (RP) LC column 12, a Waters XB Bridge™ 300 C4 column was used and a trifluoroacetic acid (TFA)-containing mobile phase of ACN:H₂O:TFA (30:70:0.1 by volume) was adopted. TFA is often used as a mobile phase modifier in the separation of protein mixtures by RP-LC to enhance chromatographic performance. TFA can adjust pH and acts like an ion-pairing agent. However, TFA is not "ESI-friendly" reagent due to its signal suppression effect. In this experiment, a 20 µL protein mixture of insulin and ubiquitin (100 µM each) was loaded for LC separation. The eluent 14 at a flow rate of 1.0 mL/min was flowed through the PEEK tube 16, and a portion of the eluent 32 (approximately 30%) was subject to ionization by DESI 40 with the spray solvent CH₃OH:H₂O:HOAc=50:50:1. As shown in the extract ion chromatograms (EIC) of FIGS. 2A and 2B, two proteins were well separated. The peak intensities for +4 insulin ion and +6 ubiquitin ion were 1.76E6 and 2.69E6, respectively. Both of the peak widths for insulin and ubiquitin were approximately 1 min. The resulting DESI-MS spectra (FIGS. 2C and 2D) also clearly display the ionized proteins with multiple charge distribution. Because the micro-hole 30 channel had a dead volume of only 0.05 µL, the portion of eluent 32 passed through the micro-hole 30 in approximately 10 ms. Therefore, DESI-MS used in this experiment offered virtually "real-time" monitoring of LC eluent 14. In addition, as shown in FIGS. 2A and 2B, there was no sample leftover effect for DESI signal.

Figures 1, 2C:
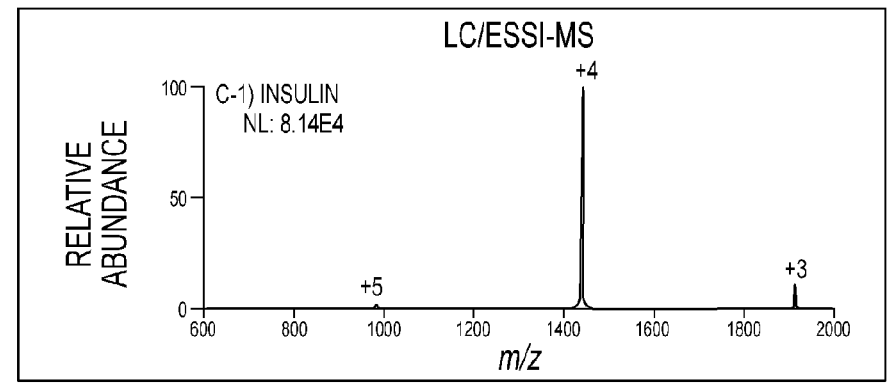
Figures 1, 2D:
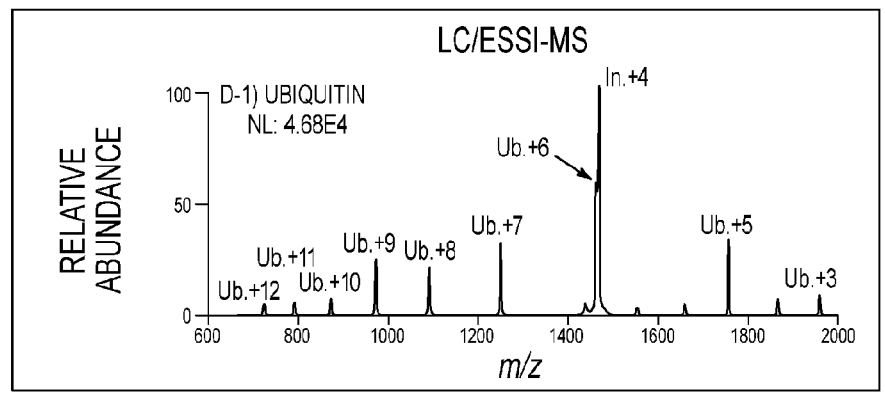

For comparison with the DESI detection used in this experiment, ESSI was also used to detect the LC separated analytes. In this LC/ESSI-MS experiment, the LC eluent flow rate was reduced to 10 µL/min (an optimized flow rate for ESSI ionization) using a commercial splitter because a high flow of LC eluent at 1.0 mL/min would flood the ESSI ion source. Other experimental conditions were kept the same as that of LC/DESI-MS. However, splitting using the commercial splitter caused peak broadening and low sensitivity due to increased dead volume. As revealed by the collected ESSI-MS spectra shown in FIGS. 2A-1 and 2B-1, the two proteins' EIC profiles had overlap in the retention time window of 8-10 min. The retention times for both proteins were both delayed by about 4 min in comparison to DESI detection, which was likely caused by the increased dead volume from the splitting used in this LC/ESSI-MS experiment. Also, the two EIC peaks of the proteins were much wider than those of LC/DESI-MS, which lasted about 4 minutes (FIGS. 2A-1 and 2B-1). In this case, even though the insulin could be separately detected between the retention time of 7-8 min (FIG. 2C-1), the ubiquitin MS spectrum averaged from the retention of 8-11 min (FIG. 2D-1) showed the presence of insulin peaks. Because of the peak broadening, the ESSI-MS spectra (FIGS. 2C-1 and 2D-1) also displayed lower ion intensities that those of DESI-MS spectra (FIGS. 2C and 2D). The same intensity trend can be seen in the EIC profiles as well (FIGS. 2A, 2B, 2A-1, and 2B-1).

Figures 2, 2A:
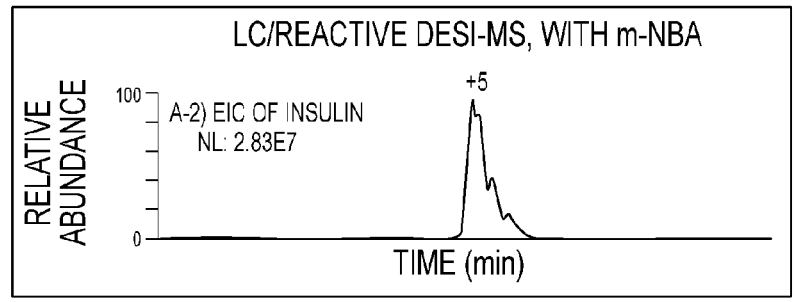
Figures 2, 2B:
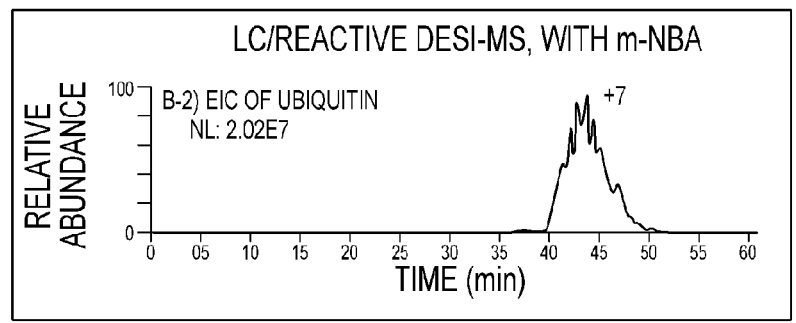
Figures 2, 2C:
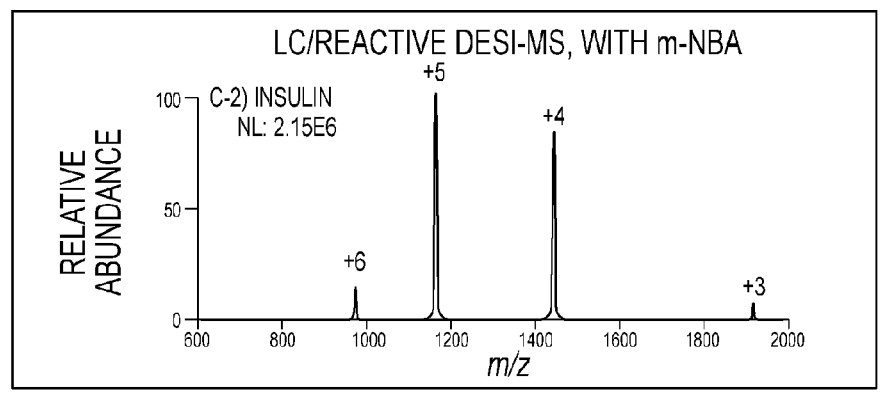
Figures 2, 2D:
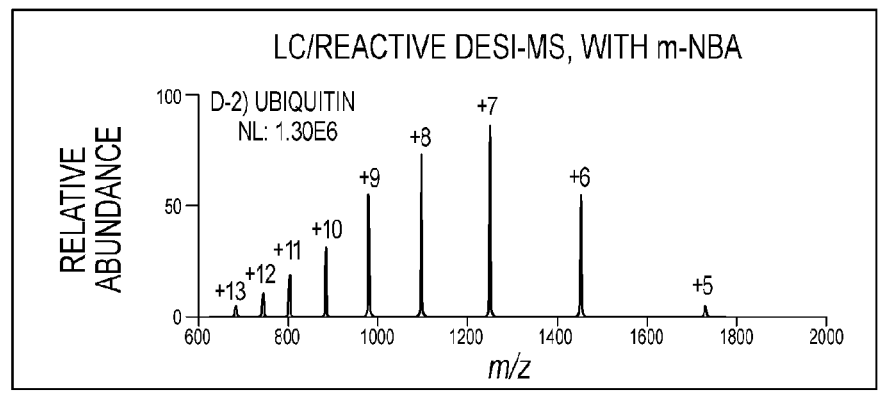
Figure 2A:
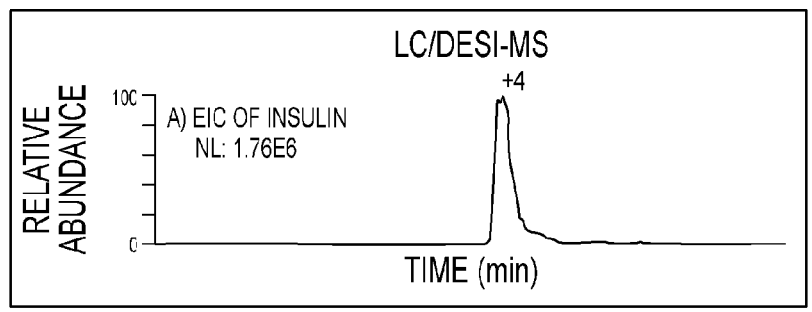
Figure 2B:
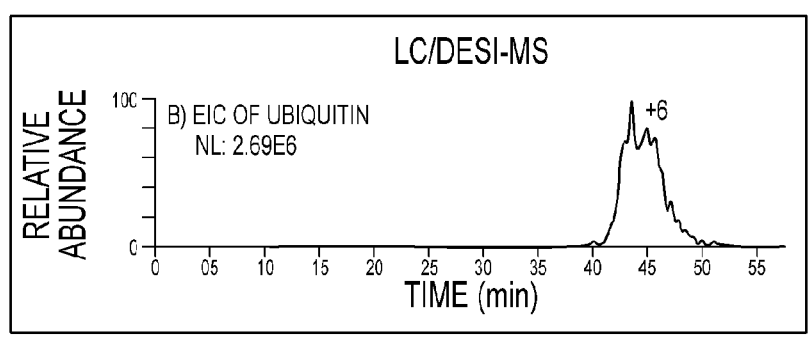
Figure 2C:
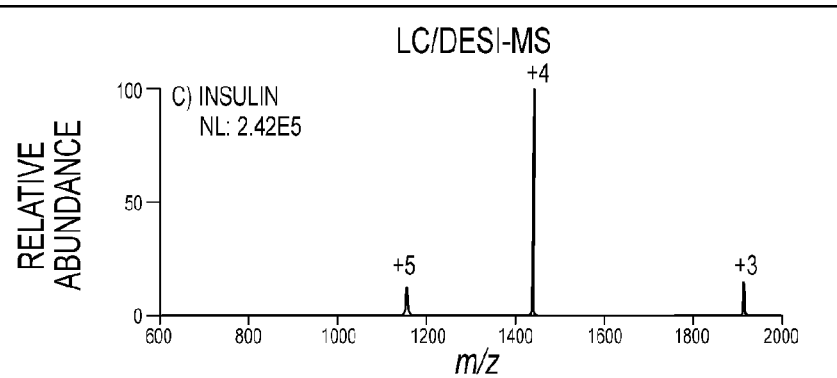
Figure 2D:
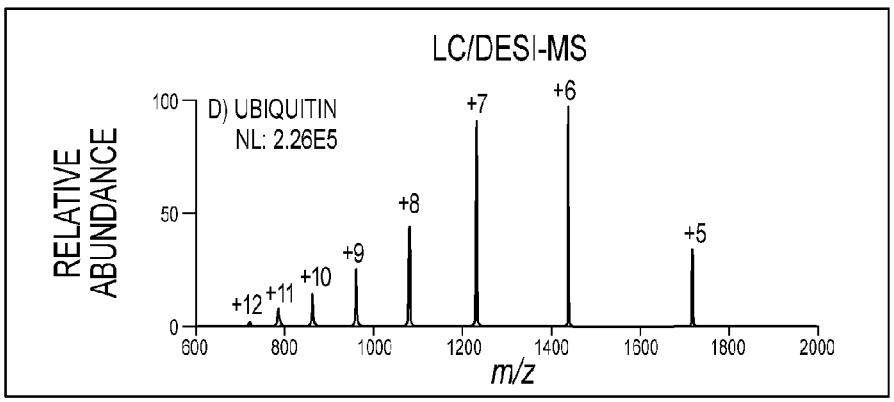

In addition to the "near real-time" monitoring benefit, the LC/DESI-MS has an additional advantage for introducing online derivatization using reactive DESI. Reactive DESI, in which a chosen chemical reagent is doped with the DESI spray solvent, is applicable in this LC/DESI-MS method, for selective derivatization of separated analytes following the chromatographic separation. Such an online-derivatization would not introduce extra dead volume, as the derivatization occurs during ionization and no post-column Tee is needed to introduce derivatizing reagents. In this study, the DESI spray solvent was changed to 50 mM m-NBA in $CH_3OH:H_2O$:HOAc (50:50:1 by volume) to effect "supercharging" proteins eluted from the LC column (i.e., increasing the protein ion charge numbers). The charge enhancement for proteins by supercharging is of great value for further structural analysis via top-down approaches using electron-based tandem MS techniques for increasing the ECD or ETD fragmentation efficiency. It is known that m-NBA is an effective supercharging reagent. Indeed, as m-NBA was doped in the DESI spray, the maximum charge state of insulin shifted from +4 to +5 (FIG. 2C-2), and the average charged state of insulin shifted from +3.9 to +4.6 (FIG. 2C-2) compared to the ESSI data (FIG. 2C-1). Likewise, the maximum charge state of ubiquitin shifted from +12 to +13 (FIG. 2D-2) and the average charged state of ubiqutin shifted from +6.8 to +8.0 (FIG. 2D-2) compared to the ESSI data (FIG. 2D-1). The enhanced charges of the detected protein ions would benefit subsequent top-down analysis if in need. The EICs spectra (FIGS. 2A-2 and 2B-2) also display good separation of both proteins. Both peak widths and retention times in this LC/reactive DESI-MS are similar to those obtained using LC/DESI-MS (FIGS. 2A and 2B), which demonstrates the good reproducibility of this DESI interface for LC/MS combination. Interestingly, the signal of resulting protein ions in this LC/reactive DESI-MS (FIGS. 2A-1 and 2B-1) is much higher than those obtained using LC/ESSI (FIGS. 2A-1 and 2B-1) and LC/DESI-MS (FIGS. 2A and 2B).

Example 2

Figure 3A:
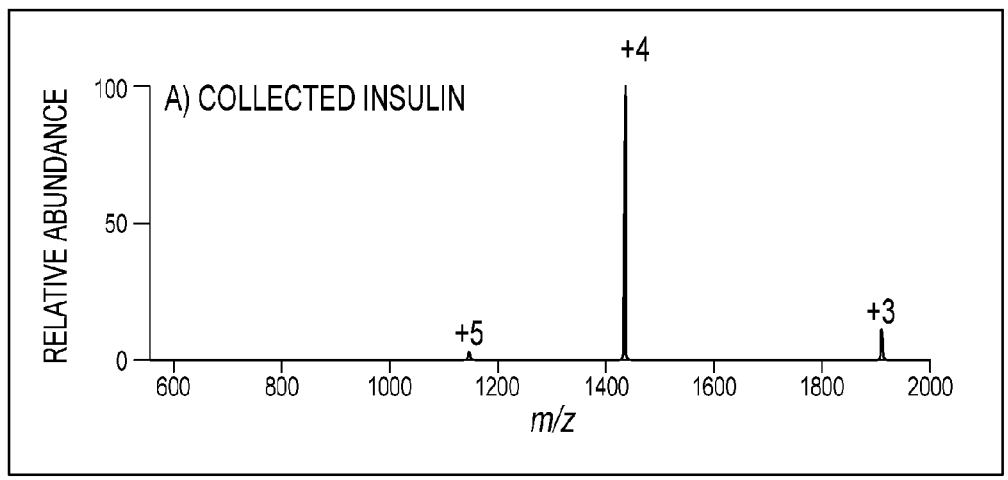
FIGS. 3A and 3B are spectra of collected insulin and collected ubiquitin analyzed using ESSI-MS according to the experiment of Example 2.
Figure 3B:
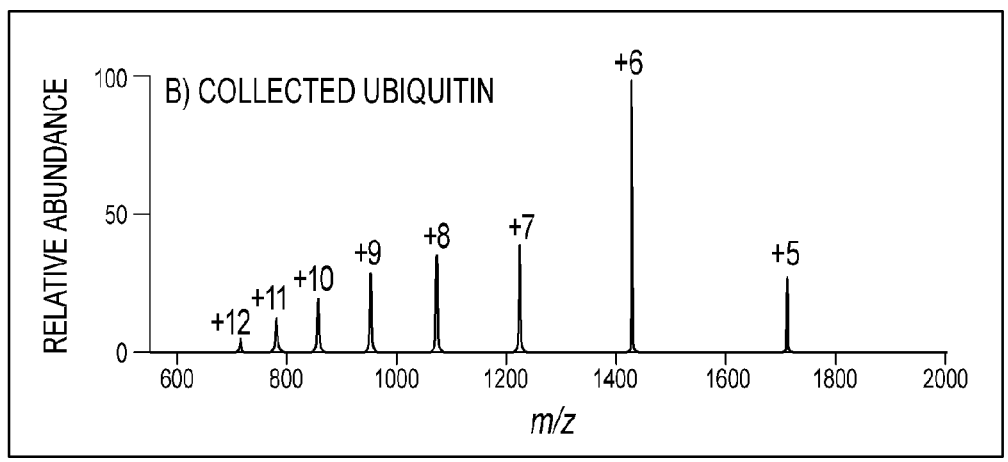

Besides the analytical merit of this DESI interface, another important feature of this method is to collect LC-separated samples following LC/MS analysis. Indeed, a major portion of proteins eluted out from PEEK tube 16 (70%) were online collected, with the aid of online DESI monitoring with negligible time delay, as mentioned above. Re-analysis of the two collected sample by ESSI gave rise to ESSI-MS spectra of insulin and ubiquitin without cross-talking (as shown in FIGS. 3A and 3B, respectively), confirming that the two samples were completely separated and successfully collected.

Example 3

In consideration with the fact that a relatively large amount of eluent 14 (30%) was used for DESI-MS analysis, a micro-hole 30 with a smaller inner diameter $d_m$, specifically 100 μm was drilled on the PEEK tube 16. With the experimental conditions, only about 4% of the eluent 32 was subject to DESI ionization in this case so that the remaining 96% of the eluent 34 would be collected, increasing the collection yield. An experiment was further conducted to compare the performance of the two different PEEK tubes 16 (one with a 100 μm inner diameter and a second with a 350 μm inner diameter), using a mixture of insulin and ubiquitin as a test sample. The results showed that, while the two PEEK tubes 16 led to similar EIC spectra (i.e., similar peak width and retention times), the signal of the smaller micro-hole 30 gave rise to even better sensitivity. Successful sample collection was also obtained using the PEEK tube 16 with the smaller micro-hole 30 with collection yield over 94% for protein samples (i.e., fairly close to the theoretical yield of 96%).

Example 4

Figure 4A:
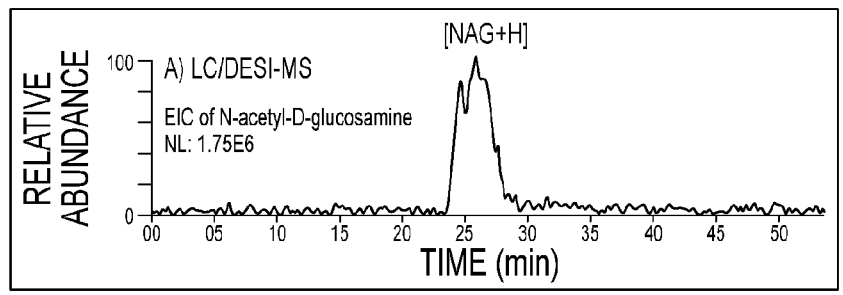
FIGS. 4A-4F are extracted ion chromatograms showing the results of the experiment of Example 4.
Figure 4B:
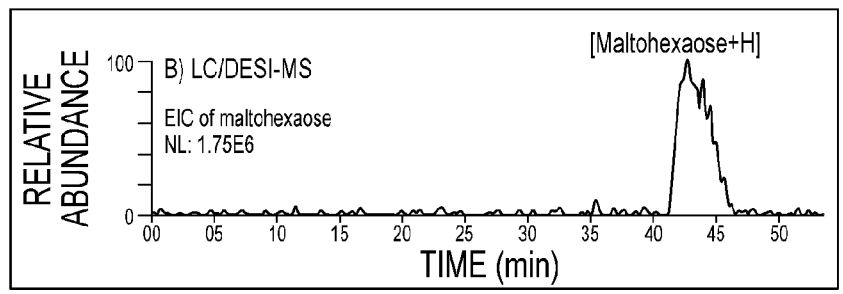
Figure 4C:
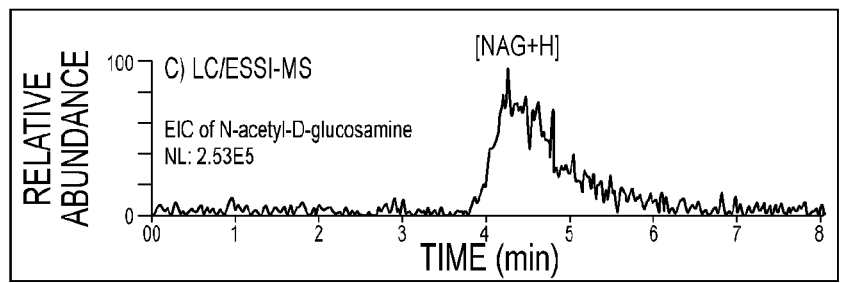
Figure 4D:
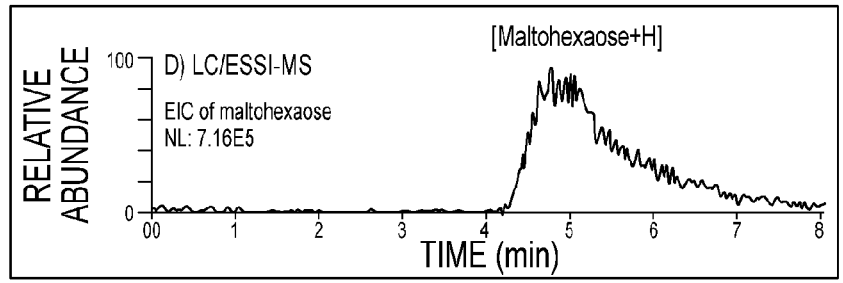
Figure 4E:
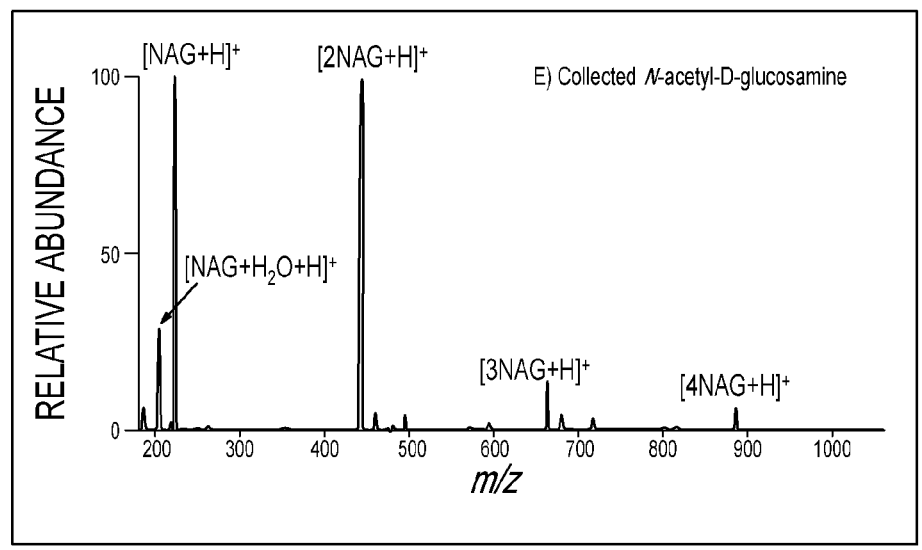
Figure 4F:
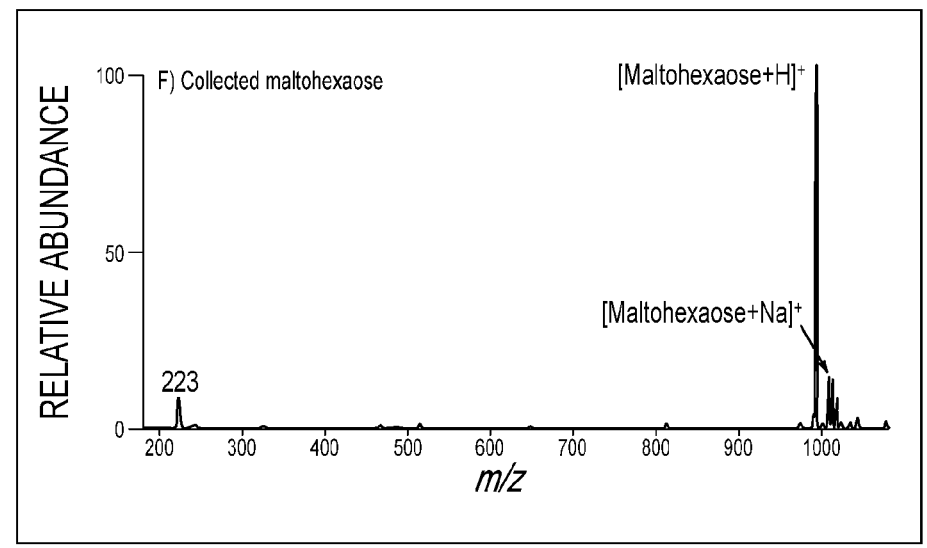

Conventionally, in a preparative LC experiment, collection of LC-separated eluent 14 is often facilitated by a UV detector placed between the LC column 12 and the liquid sample collector 24. However, this approach is limited to UV adsorption compounds with chromophores. For UV adsorption compounds without chromophores, derivatization is needed, which is time consuming and troublesome. In the present invention, by using online DESI monitoring instead, this problem is solved, as MS is a universal detector. As a demonstration, a saccharide mixture consisting of 2.5 mM N-Acetyl-D-glucosamine (NAG) and 2.5 mM maltohexaose was chosen as a test sample because saccharides often have no or weak UV absorption. An Agilent ZORBAX ODS column was employed in this LC/DESI-MS experiment. As shown in FIGS. 4A and 4B, the recorded EIC spectra of two saccharides, N-Acetyl-D-glucosamine and maltohexaose were well separated. Again, in contrast, when ESSI was used (via 1:49 splitting), wider peaks with lower intensities resulted. As shown in FIGS. 4C and 4D, the detection of two saccharides by ESSI was delayed about 2 min in comparison to DESI detection (FIGS. 4A and 4B), and the peaking broadening was also observed. As a result, the EIC of N-Acetyl-D-glucosamine and maltohexaose overlapped with each other (FIGS. 4C and 4D), and the ESSI-MS also showed the presence of both NAG and maltohexaose (data not shown). In addition, lower intensities in ESSI detection compared with DESI were observed, which likely resulted from both peak broadening and low ionization efficiency due to difficulty in desolvation during ESSI ionization because pure water was used as the mobile phase. In the LC/DESI-MS, the major portion of saccharides out from PEEK tube 16 was collected and re-tested with ESSI, which clearly show the good separation of two purified saccharide molecules (FIGS. 4E and 4F).

Example 5

Figure 5A:
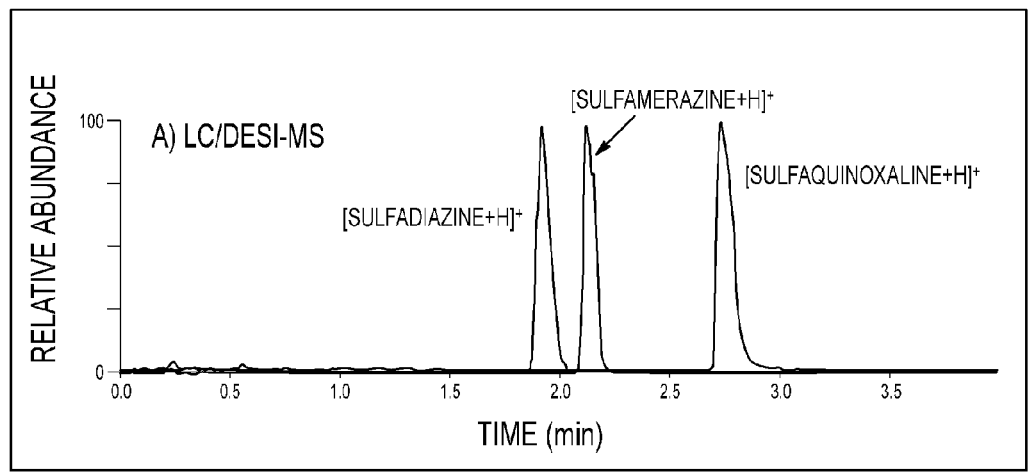
FIGS. 5A and 5B are extracted ion chromatograms showing the results of the experiment of Example 5.

In addition to LC separation using regular analytical columns, the compatibility of the splitting method described herein to monolithic column-based ultra-fast LC separation was also examined. Monolithic columns can reach extremely high flow rates (up to 9 mL/min) which could perform high throughput and maintain good separation close to ultra-high performance LC without causing significant back pressure. Thus, the separation can be completed in a short period of time. A mixture of sulfonamides, including sufadiazine, sufamerazine, and sulfaquinoxaline (100 μM each), was chosen as a test sample for demonstration of the application of the splitting method to the monolithic column-based ultra-fast LC separation. An Onyx™ C19 monolithic column and a PEEK tube 16 with a micro-hole 30 having an inner diameter $d_m$ of 100 μm was used. As shown in the EIC spectrum recorded by DESI-MS (FIG. 5A), the sufadiazine, sulfamerazine, and sulfaquinoxaline were all separated and eluted within 3 min. In comparison, when a regular reversed-phase C19 column with an elution flow rate of 1 mL/min was used for the separation of the same mixture, the total elution time needs to be more than 11 min (data not shown). This result shows that the high flow rate helps fast elution and separation.

Figure 5B:
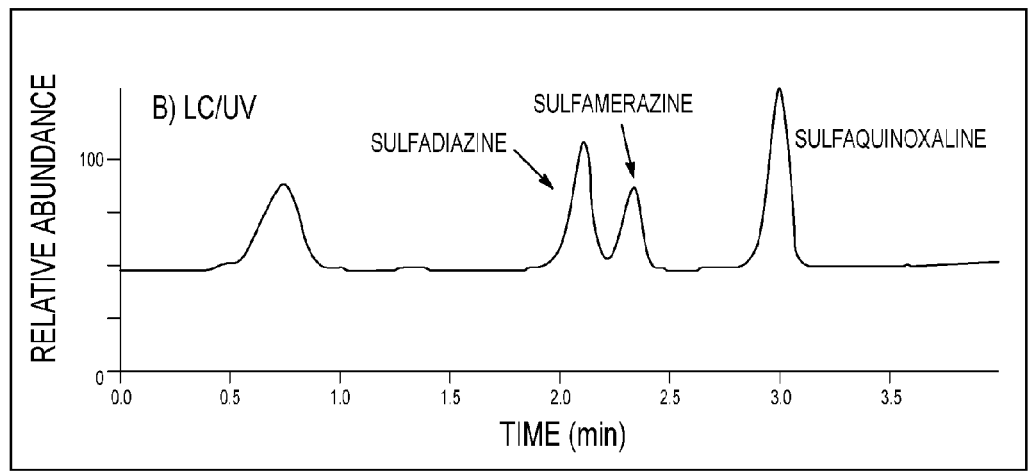

The chromatograph was also recorded using a UV detector (detection wavelength: 254 nm) for comparison (FIG. 5B). The DESI-MS recorded chromatogram has slightly better resolution than that recorded by UV detector. For instance, there is about a 10% overlap of the sulfadiazine and sulfamerazine peaks in FIG. 5B, while the two peaks are well resolved in the DESI-MS recorded chromatogram. This might be also due to the overall small dead volume involved in the splitting method. However, an attempt to split the high flow eluent of 4 mL/min down to 10 µL/min for ESSI-MS detection by the commercial splitter caused column failure due to high back pressure that exceeded a tolerance of the monolithic column used. In contrast, in the present splitting method in conjunction with DESI-MS detection, there is no back pressure issue as the PEEK tube 16 used for splitting has a micro-hole 30 that is not blocked or linked with another device.

As explained above, the present invention presents a novel and versatile LC/MS interface for LC/MS applications, which is built on new LC eluent splitting and ambient ionization techniques. The interface provides a coupling for LC and MS that uses DESI or another method of ambient ionization to provide direct ionization of analytes with little or no sample preparation. The interface between the LC column 12 and the mass spectrometer 60 allows for fast MS detection of analytes after LC separation. Moreover, the present invention provides for synchronous MS detection and sample collection of non-ionized LC eluent 34. By not introducing back pressure, the present invention allows for almost real-time monitoring of LC-separated analytes and allows for high yield collection.

This has been a description of the present invention along with the various methods of practicing the present invention. However, the invention itself should only be defined by the appended claims.

What is claimed is:

1. An apparatus for analyzing a liquid sample, the apparatus comprising:
   a fluid conduit for defining a flow passage and configured to supply the liquid sample, the fluid conduit having an outer surface and a micro-hole through the outer surface into the flow passage;
   an ambient ionizer configured to generate a charged solvent and to direct the charged solvent toward the micro-hole at the outer surface; and
   a mass spectrometer having a sample entrance adjacent the micro-hole.

2. The apparatus of claim 1, wherein the flow passage has an inner diameter greater than an inner diameter of the micro-hole.

3. The apparatus of claim 1, wherein the flow passage has an inner diameter less than an inner diameter of the micro-hole.

4. The apparatus of claim 1, wherein an inner diameter of the flow passage ranges from approximately 10 µm to approximately 1000 µm.

5. The apparatus of claim 1, wherein an inner diameter of the micro-hole ranges from approximately 10 µm to approximately 350 µm.

6. The apparatus of claim 1, wherein the fluid conduit has a wall through which the micro-hole is drilled, the wall having a thickness ranging from approximately 10 µm to approximately 1000 µm.

7. The apparatus of claim 1, wherein the fluid conduit is coupled to an outlet of a liquid chromatography column.

8. The apparatus of claim 7, wherein the liquid chromatography column comprises one of a reversed phase column, a normal phase column, a monolithic column, a size-exclusion column, an ion exchange column, and an ultra performance liquid chromatography column.

9. The apparatus of claim 7, wherein the outlet of the chromatography column and the micro-hole are horizontally separated by approximately 1 mm to approximately 3 cm.

10. The apparatus of claim 1, wherein the fluid conduit is composed substantially of polyaryletheretherketone.

11. The apparatus of claim 1, wherein the ambient ionizer performs one of desorption electrospray ionization, direct analysis in real time, high energy particles ionization, and laser desorption ionization.

12. A method of analyzing a liquid sample, the method comprising:
    supplying the liquid sample through a fluid conduit having an outer surface, a flow passage, and a micro-hole through the outer surface into the flow passage, such that a first portion of the liquid sample exits the fluid conduit through the micro-hole and a second portion of the liquid sample continues through the fluid conduit;
    directing a charged solvent to the first portion of the liquid sample toward the micro-hole at the outer surface thereby ionizing the first portion of the liquid sample to form an ionized portion;
    directing the ionized portion to a mass spectrometer; and
    collecting the second portion of the liquid sample without ionizing the second portion.

13. The method of claim 12, further comprising:
    directing a supply of the liquid sample from a liquid chromatograph into the fluid conduit.

14. The method of claim 12, wherein a splitting ratio of the first portion of the liquid sample to the second portion of the liquid sample ranges from approximately 4:96 to approximately 3:7.

15. The method of claim 12, wherein the charged solvent is generated by one of desorption electrospray ionization, direct analysis in real time, high energy particles ionization, and laser desorption ionization.

16. The method of claim 12, wherein the time required for the first portion of the liquid sample to exit the fluid conduit through the micro-hole is less than or equal to approximately 10 ms.

17. The method of claim 16, wherein the time required for the first portion of the liquid sample to exit the fluid conduit through the micro-hole is less than or equal to approximately 6 ms.

18. The method of claim 12, wherein the second portion of the liquid sample is introduced into an analyzer.

* * * * *